United States Patent [19]
Sliwa, Jr. et al.

[11] Patent Number: 5,749,364
[45] Date of Patent: May 12, 1998

[54] METHOD AND APPARATUS FOR MAPPING PRESSURE AND TISSUE PROPERTIES

[75] Inventors: John W. Sliwa, Jr., Los Altos; Michelle L. Jung, Campbell; Paul E. Chandler, Santa Cruz; Amin M. Hanafy, Los Altos; David J. Napolitano, Menlo Park, all of Calif.

[73] Assignee: Acuson Corporation, Mountain View, Calif.

[21] Appl. No.: 667,765

[22] Filed: Jun. 21, 1996

[51] Int. Cl.$^6$ .................................................. A61B 8/00
[52] U.S. Cl. .................................................. 128/662.02
[58] Field of Search .................. 128/660.02, 662.02, 128/774, 672, 713; 424/9.5, 9.51, 9.52

[56] References Cited

U.S. PATENT DOCUMENTS

| | | | |
|---|---|---|---|
| 3,640,271 | 2/1972 | Horton | 128/2.05 D |
| 4,316,391 | 2/1982 | Tickner | 128/662.02 |
| 5,195,520 | 3/1993 | Schlief et al. | 128/660.02 |
| 5,285,788 | 2/1994 | Arenson et al. | 128/662.02 |
| 5,425,366 | 6/1995 | Reinhardt et al. | 128/662.02 |
| 5,447,161 | 9/1995 | Blazek et al. | 128/677 |

FOREIGN PATENT DOCUMENTS

WO96/09793  4/1996  WIPO ............... A61B 8/00

OTHER PUBLICATIONS

Blinov, A. V. and Selivanov E. P., *A Measuring and Computing Method and Device For Determining Arterial Blood Pressure Parameters N Humans*, Measurement Techniques vol. 37 No. 4 pp. 466–470 (1994).

Church, C. C., *The Effects of an Elastic Solid Surface Layer on the Radial Pulsations of Gas Bubbles*, J. Acoust. Soc. Am. 97 (3), pp. 1510–1521 (Mar. 1995).

Gensane, M., *Bubble Population Measurements with a Parametric Array*, J. Acoust. Soc. Am. 95 (6), pp. 3183–3190 (Jun. 1994).

Gottlieb, S. et al., *Effect of Pressure on Echocardiographic Videodensity from Sonicated Albumin: An In Vitro Model*, J. Ultrasound Med. 14:109–116 (1995).

Ishihara, K. et al., *New Approach to Noninvasive Manometry Based on Pressure Dependent Resonant Shift of Elastic Microcapsules in Ultrasonic Frequency Characteristics*, Japanese J. of App. Physics vol. 27 Supp. 27 pp. 125–127 (1988).

Iyriboz, Y. and Hearon, C. M., *A Proposal for Scientific Validation of Instsruments for Indirect Blood Pressure Measurement at Rest, During Exercise, and in Critical Care*, Journal of Clinical Monitoring vol. 10 No. 3 pp. 163–177 (May 1994).

Jong, N. de et al., *Absorption and Scatter of Encapsulated Gas Filled Microspheres: Theoretical Considerations and Some Measurements*, Ultrasonics vol. 30 No. 2 pp. 95–103 (1992).

Leighton, T.G., *Transient Excitation of Insonated Bubbles*, Ultasonics vol. 27 No. 1 pp. 50–54 (Nov. 1989).

Medwin, H., *Counting Bubbles Acoustically: A Review*, Ultrasonics vol. 15 No. 1 pp. 7–13 (Jan. 1977).

(List continued on next page.)

*Primary Examiner*—George Manuel
*Attorney, Agent, or Firm*—Hopkins & Carley

[57] ABSTRACT

The invention disclosed relates to a novel method of mapping and presenting fluid pressure information within a living body utilizing changes in acoustic behavior of microbubbles situated in a bodily fluid such as blood. Differences in the returned acoustic spectra from the microbubbles are related by an algorithm to fluid pressure which is colorized and presented in a manner similar to Doppler imaging. In a further aspect of the invention, the work output of an organ such as the heart may computed from the blood pressure information in association with flow information obtained through Doppler related imaging, which then, is presented in a colorized fashion. In a still further aspect, an improved method of assessing the health of tissue is disclosed utilizing changes in the acoustic spectra of microbubbles infused in the tissue in response to palpitation.

54 Claims, 10 Drawing Sheets

OTHER PUBLICATIONS

O'Brien, E. and Fitzgerald, D., *The History of Blood Pressure Measurement*, Journal of Human Hypertension vol. 8 pp. 73–84 (1994).

Wu, J. and Shung K., *Nonlinear Energy Exchange Among Harmonic Modes and its Applications to Nonlinear Imaging*, J. Acoust. Soc. Am. vol. 88 (6), pp. 2852–2858 (Dec. 1990).

METHOD AND APPARATUS FOR MAPPING PRESSURE AND TISSUE PROPERTIES

FIELD OF INVENTION

This present invention relates generally to the field of medical sonography. In particular, it pertains to a relatively non-invasive method of mapping and presenting bodily fluid pressure in at least two dimensions and to an enhanced method of detecting tumorous tissue.

BACKGROUND OF THE INVENTION

Medical ultrasound imaging provides a non-ionizing, non-radioactive, and relatively inexpensive method to image the internal body as compared to other imaging technologies such as X-ray, MRI, and CATSCAN. Ultrasound systems typically operate by transmitting a sweeping beam of high frequency sound waves from a transducer and receiving reflected waves from tissue interfaces which are processed and formed into an image. Very good images of various soft tissues can be obtained. For this reason, applications for ultrasound have extended to virtually all medical specialties including cardiology, obstetrics, pediatrics, surgery, neurology, and radiology.

A primary focus in cardiology ultrasound is in achieving enhanced real time images of the heart. Obtaining clear images of the heart chambers, particularly at the wall edges, has been difficult to achieve with conventional ultrasound imaging modes. This is because the acoustic reflectivity of the heart tissue and neighboring blood can be somewhat similar and are only minimally reflective. Significant recent improvements have come with the introduction of contrast agents into the blood that are highly acoustically reflective causing the blood to show up as bright (strong speckle scatterer) relative to the much darker chamber wall tissue. In this manner, the chamber walls can now be clearly seen.

As known to those in the art, echo cardiographic contrast agents, also referred to as microbubbles or bubbles are typically biocompatible polymer microcapsules (0.5 to 2 microns diameter). Many types of these particles are hollow and are filled either with a gas, a liquid or a second polymer or gel. Polymers used for these purposes can be organic, synthetic or semisynthetic in origin and typically eventually dissolve in the blood or are absorbed into tissue and passed out through the liver. Contrast enhancement due to microbubbles may be exhibited by one or both of backscatter or attenuation mechanisms (acoustic absorption). The usual mode of image enhancement occurs from an increase in reflected signal over a broad frequency spectrum thereby intensifying the acoustic contrast between the region containing the microbubbles and the surrounding tissue which typically contains no bubbles. One may also selectively image harmonic returned signals known to originate only in the contrast agent particles.

It has been known to use ultrasound in combination with microbubbles to measure pressure in a liquid in a closed test fixture. Such efforts rely on the fact that the bubbles, when suspended in the liquid, naturally resonate at a specific pressure-dependent frequency when subjected to excitation sound waves. The bubbles are affected by the incoming acoustic signal in a predictable manner which is a monotonic function of the effective local liquid pressure. That is, the incoming acoustic signal, upon impinging on the bubbles, predictably excites a returned signal as determined by the local fluid pressure being experienced by the bubbles at that moment. Whether the bubbles are gas or polymer filled, thin or thick walled, they always see a frequency pressure dependence of some monotonic sort. Since the resonant frequency for a gas bubble can be expressed as:

$$f=(1/\pi d)(3kP/p)^{1/2}$$

where d is diameter of bubble, k is specific heat of microbubble gas, P is ambient fluid pressure, and p is density of ambient fluid. It can be seen that resonant frequency is proportional to the square root of pressure and inversely proportional to bubble diameter.

In addition to bubble reflected signals, a well known nonlinear characteristic of resonated bubbles is the generation of super-harmonics and sub-harmonics which are multiples of the fundamental excitation frequency. The excited harmonic modes are frequency shifted with respect to the fundamental driving frequency. This permits the convenient situation wherein transmission near the resonant fundamental frequency would result in the generation of returned harmonics coming from the contrast agent well out of range of the original transmission spectrum. By way of example, a fundamental resonant mode at 3 MHz will excite the 6 MHz and 12 MHz nonlinear harmonic modes etc., in addition to associated sub harmonics. A receiver may then be configured to selectively receive the 6 MHz excited nonlinear mode to selectively display a contrast-agent enhanced image with high discrimination. This provides increased signal to noise since the received signal from the contrast agent is well out of range of the transmitted signal thereby eliminating potential interference. Signals coming from tissue or fluid not containing contrast agents are within the original spectrum and can be ignored. The aforementioned procedure (lacking the pressure aspect) is collectively known as "Harmonic Imaging" and has been used in the prior art as a method of image enhancement using contrast agents.

Additionally, microbubbles have been used to provide contrast enhancement of tissue perfusion wherein a perfusing contrast agent is imaged. The detection of malignant tumors in body tissue through the use of non-invasive ultrasound imaging has been an area of intense interest over the years. The analysis of tissue properties has been done with common ultrasound image modalities such as B-mode gray scale imaging, pulse-echo spectral Doppler and Color Doppler modalities. Color Doppler Imaging has the advantage of being able to clearly display relative motion as colorized mapped representations Color Doppler has been successfully used to detect a class of tumors which grows very fast and requires profuse vascularization. In profusely vascularized tumorous tissue there is substantial excess blood flow motion in the region. Tumors of this type tend to be easy to locate using Color Doppler but these constitute only a fraction of all tumors (about 5%). In general, it has frequently proven difficult to detect tumors using conventional ultrasound and Doppler techniques, since the contrast between many tumors and their surrounding tissue is poor in presently existing imaging modes. The subjective nature of tumor detection in ultrasound imaging often requires the application of biopsies to complete the diagnosis which can be uncomfortable, expensive and time consuming.

Ultrasound has been tried in other ways to distinguish tumors or growths from healthy tissue. One method that has been suggested to detect growths, such as calcium rich growths that are harder than the surrounding tissue, is to subject the examination region to low frequency vibration (approximate range of 200–400 Hz). Since the tumor or growth has slightly different mechanical properties, such as density or elastic constant, than the surrounding healthy tissue, it has been found that at the low frequency, the tumor or growth will vibrate at the low frequency slightly out of phase with the adjacent healthy tissue. Color Doppler modalities can be utilized to achieve a colorized depiction of the se out-of-step relative motions. The relative motions may be colorized such that the tumor or growth is shown in red and the surrounding tissue in blue, for example. This method has proved more difficult in practice than in theory, especially for smaller tumors or growths since they increasingly tend to mechanically act similarly to the surrounding tissue. Another problem with this approach is that it is limited to low-frequency resolution due to the use of low frequency Doppler thereby rendering tiny tumors invisible. A further problem is that healthy surrounding tissue, if relatively stiff itself, can either mask the tumor or make it appear more diffuse.

In view of the foregoing, an improved ultrasound modality is disclosed that can be used solely or in association with other modalities such as B-mode gray scale, Pulse-Echo Spectral and Color Doppler for the mapping and presentation of bodily fluid pressure and the computation of flow-work. A further aim is directed to an improved method for detecting tumors, or other abnormal growths or deposits, that does not rely on their mechanical motion characteristics, therefore, permitting the detection of a much larger range in size of tumors, growths, and lesions.

SUMMARY OF THE INVENTION

In a first embodiment of the present invention, a method of mapping and presenting fluid pressure information within a living body utilizing changes in acoustic behavior of microbubbles is disclosed. The method includes the steps of introducing acoustically responsive microbubbles into the body that are suspended, at least in part, in a body fluid such as blood. High frequency sound waves are applied to the region containing the microbubbles and an acoustic spectrum returned from the region. A fluid pressure parameter is determined in response to at least one characteristic of the acoustic spectrum and the fluid pressure parameter is mapped in at least two dimensions. It can then be colorized or otherwise graphically presented for display for a visually efficient depiction of dynamic fluid pressure.

In a further aspect of the first embodiment, a method of mapping, recording, and graphically presenting in at least two dimensions the hydraulic or hemodynamic work performed by a bodily organ, such as the heart, is disclosed. The work or energy expended or absorbed by an organ or vasculature is computed from fluid pressure information and flow information obtained by Doppler techniques where the pressure information is obtained indirectly from the acoustic behavior of microbubbles suspended in the fluid. The work may then be colorized where, for example, the areas of the organ expending relatively high amounts of energy may be represented in red and areas corresponding to relatively low energy output may be represented in blue, and intermediate levels are expressed by color gradation in between red and blue. The colorized work information may then be presented solely or in combination with other ultrasound modalities such as B-mode gray scale and Spectral and Color Pulse Doppler modes. The combination of imaging modes may also be displayed as a three dimensional dynamic colorized image. The net work being done by or on a selected control volume may also be reported on the display as a scalar parameter.

In a second embodiment of the present invention, a method of assessing the health of bodily organs and bodily tissue is disclosed. Microbubbles are infused into both healthy tissue and tumor tissue in which high frequency sound waves from an ultrasound transducer are applied to the region containing the microbubbles. Further, an external probing low frequency or static wave is applied to the region such that the microbubbles in the tumorous tissue display different acoustic pressure responses than adjacent bubbles in healthy tissue due to the differing permeabilities or hardnesses of the tumorous tissues. The relative differences can then be colorized and presented in at least a two dimensional mapping to the user for a more visually efficient mode of tumor or tissue anomaly detection.

DETAILED DESCRIPTION OF THE PREFERRED EMBODIMENTS

Figure 1A:
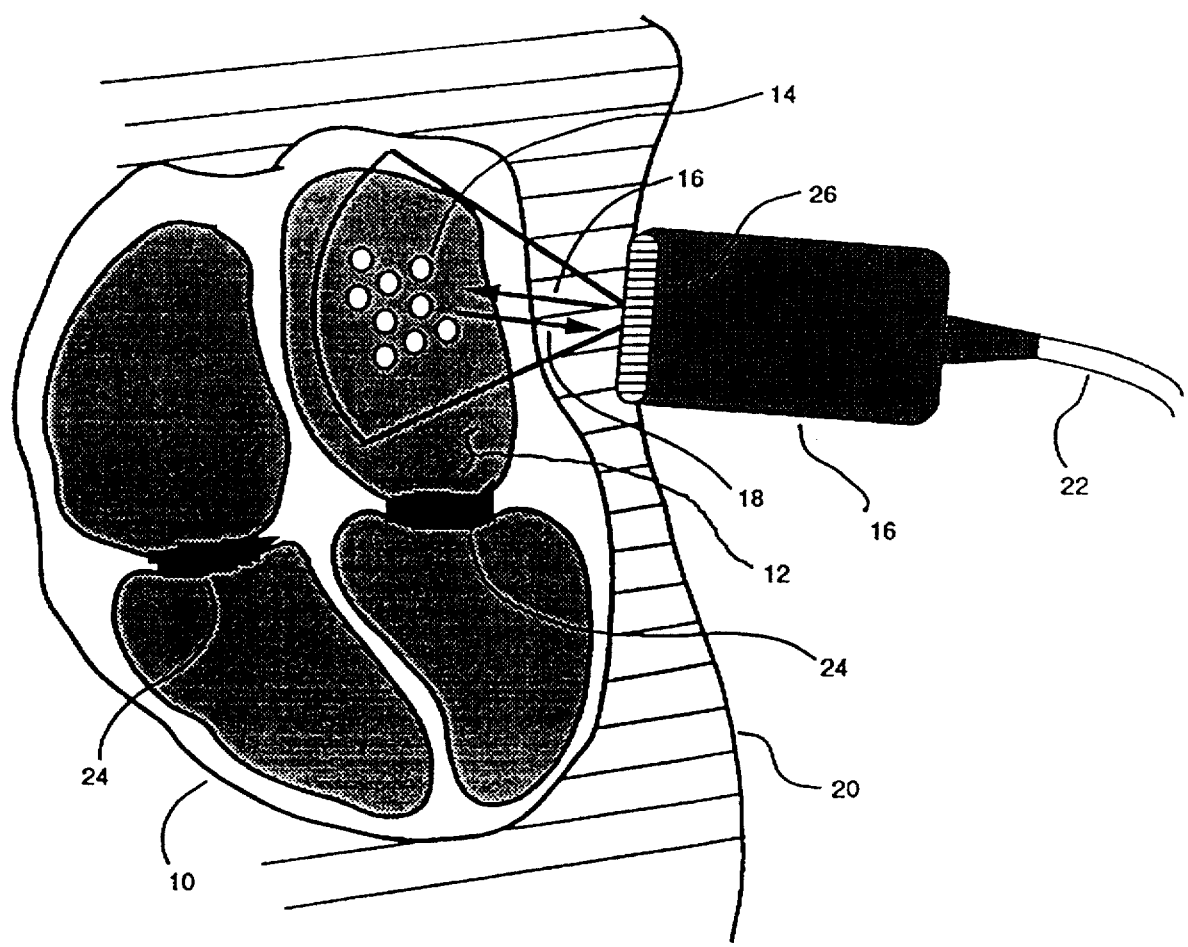
FIG. 1A is a diagrammatic view of a microbubble population in a heart chamber for improved contrast ultrasound images.

This invention is directed to a method of mapping and presenting bodily fluid pressure in at least two dimensions and to an enhanced method of detecting tumorous tissue. In accordance with the present invention, a novel modality is discussed for the mapping and presentation of bodily fluid pressure solely, superimposed or together with a generated ultrasound tissue image. In a first embodiment, a modality is described to formulate and present a 2D or higher blood pressure map in a colorized (or otherwise graphically encoded) fashion, similar to Color Doppler imaging presentations where blood flow rate is related to color. As used herein, the term "map" will be used to represent displaying pressure-related information in at least 2 dimensions; in the preferred embodiments, colorization is used for this display. For example, it is possible to map blood pressure in an area-wise or volumetric manner possibly superimposed on or interleaved with a 2D or 3D real-time (or recorded) B-ode gray-scale ultrasound image. Thus it is possible to map the blood pressure dynamically and in color as the blood surges through the heart and its related vessels and relate the behavior of pressure gradients to tissue and organ structures. Of course, a parameter relating to blood pressure can be mapped instead of strictly mapping the blood pressure values. Accordingly, "fluid pressure parameter" as used herein will include blood (or other fluid) pressure, or parameters relating to blood (or other fluid) pressure. For example, mean pressure, peak pressure, minimum pressure, change rate of pressure etc. One may also colorize or otherwise graphically encode on the viewing display the average, mean or some variation (e.g. sigma) of the local blood pressure in a mapped format. The term "characteristic" of acoustic spectrum is used herein to refer to a feature or property of the spectrum that can be used to relate to pressure. For example, amplitude, relative temporal or spatial shifts, or area or volume of the spectrum etc. Further, the term "colorize" may also be used to include gray-scale gradation mapping in addition to color scale mapping.

A significant application of the technique of the present invention is in imaging the heart, where real time observation is particularly useful in determining the work output and efficiency of the heart, as well as any of abnormalities in pressure versus location and time in the heartbeat cycle. Although the heart is the focus of this discussion, it should be apparent to those skilled in the art that the method is applicable for imaging other internal organs such as the liver or kidneys. In these cases, the "work" may be the work done in resisting flow and in being distended by perfusion or flow. The recovered work from collapsing distended vascular or arterial structures may also be monitored. The method begins by introducing a contrast agent microbubble population into the body through the blood where they eventually reach the heart (or other organ of interest) through normal circulation. The procedure for introducing contrast agents orally or by injection into the human body for imaging purposes is well known to those skilled in the art wherein contents and amounts may vary depending on the application and specific purpose. Typically introduction is done through a catheter or syringe wherein the contrast agent is suspended in a saline solution.

Referring to FIG. 1A, a diagrammatic view of a microbubble population in a blood filled heart chamber used in conjunction with ultrasound for image enhancement is shown. A human heart 10 is shown having a blood-filled chamber 12 in which microbubbles 14 have been introduced. Heart valves 24 are also shown schematically linking respective pairs of heart chambers. An imaging ultrasound transducer 16 having a piezoelement array 26 and a connecting cable 22 is shown imaging heart 10, chamber 12 and microbubbles 14 through body surface 20. The imaging ultrasound transducer 16 is schematically shown transmitting an ingoing sound wave or wavetrain 16. The ingoing waves 16 are centered at a center frequency $f_c$.

The returned or reflected waves 18 from the bubbles 14 will be different than the ingoing waves 16. These differences will depend on the instantaneous blood pressure as well as the known effects of attenuation and frequency downshifting due to tissue attenuation. In addition to changes in ingoing spectra 16, changes may also occur in the excited nonlinear harmonic modes. Such harmonics, if present, will only typically be in returned spectra 18 as known in the art. Since it is possible to monitor any one or more characteristics of the acoustic spectra, such as returned signal amplitude, returned signal frequency and returned signal phase, it then becomes possible to associate any changes with known pressure effects. It should be noted that changes of ingoing versus returned spectra or of changes between two or more returned spectra versus time (i.e. versus temporal pressure) may be observed. It should also be emphasized that the transducer 16 may accomplish this needed temporal and spatial pressure sampling using one or more simultaneous ultrasound steered beams. For the sake of simplicity, the mentioned downshift of returning spectra due to attenuation effects, which can be easily accommodated, are ignored hereinafter.

Figure 1B:
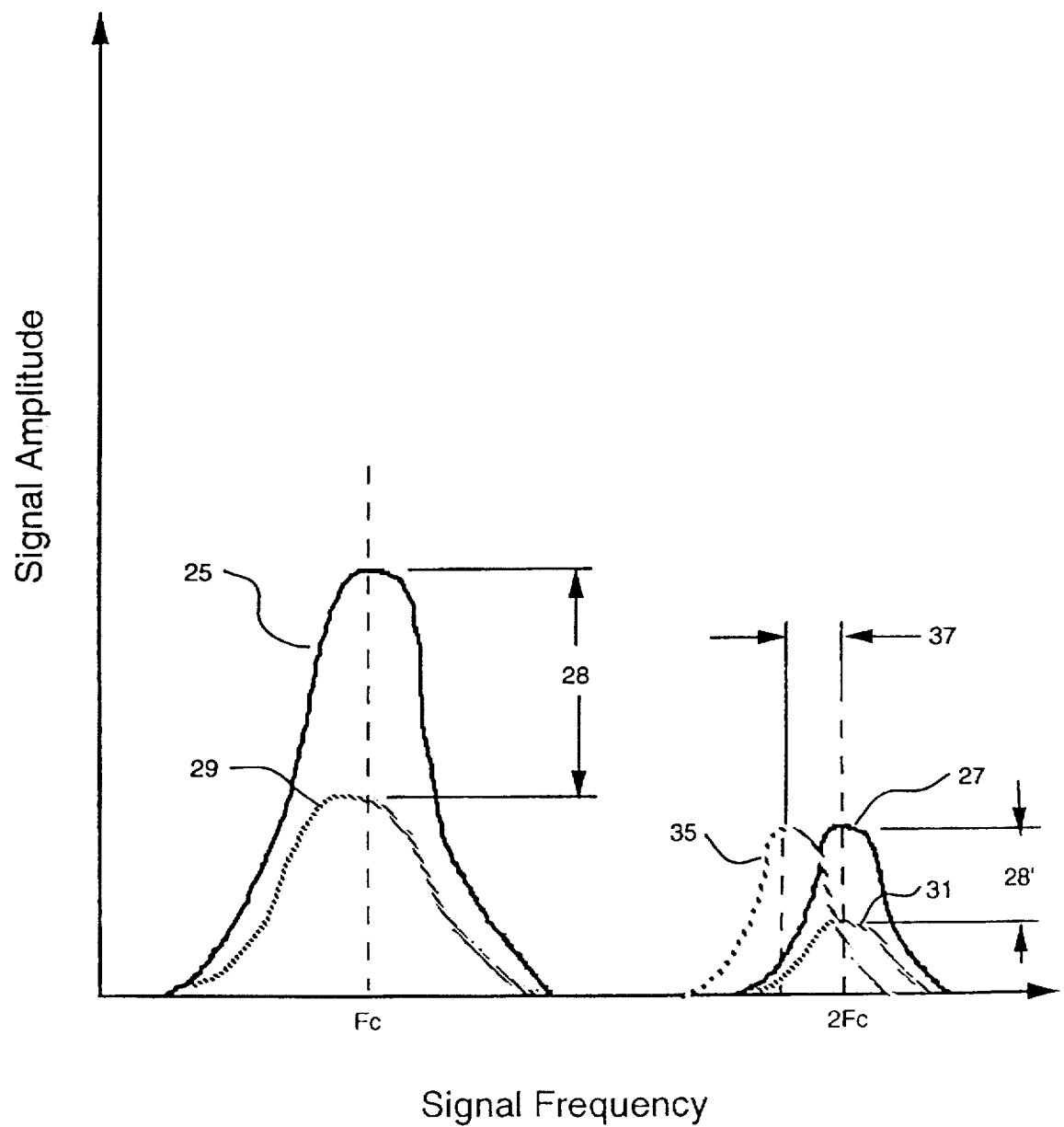
FIG. 1B is a graph of the transmitted and received acoustic spectra as a result of the ultrasound imaging arrangement in FIG. 1A and the measurement of bubble acoustic behavior changes with pressure.

FIG. 1B shows a plot of signal amplitude versus frequency for the situation previously described. In this example, the spectra shown are all returned spectra of the type 18. Specifically shown are a primary returned peak 25 centered on frequency $F_c$ as well as a returned harmonically excited peak 27 centered on frequency $2F_c$ as is known in the art. Both of these were sampled at a time $t_1$ when the blood pressure in chamber 12 was at a minimum at a given point in the chamber. In FIG. 1B, there is shown an additional primary peak 29 and additional harmonic peak 31 in phantom. It is noted that peaks 29 and 31 have reduced amplitude relative to corresponding peaks 25 and 27. These reductions in amplitude, for example, track the decrease in bubbles 14 size at a later time $t_2$ when the blood pressure at the given point reaches a maximum. Thus the known effect of contrast or returned signal reduction with bubble size reduction as a function of increased pressure is seen in FIG. 1B.

It will be apparent to those skilled in the art that in addition to (or alternatively to) monitoring amplitude changes of the type 28 and 28' of FIG. 1B one may monitor any changes in frequency or in phase. An example of such a alternative is also depicted in FIG. 1B as a frequency downshift 37 seen in the harmonic signal which consists of peak 27 at a time $t_1'$, and of peak 35 at a time $t_2'$.

It should be understood that the scope of the spectral changes is not limited in graphically mapping pressure. For example, any one of the amplitude, frequency, or phase change between sets of spectra may be utilized to map pressure. The sets of spectra may include just returning spectra at various times of the heartbeat or may also include using the ingoing spectra in comparison to each returned spectra. Also, a comparison of the spectral changes seen in two pairs of spectra versus time (and therefore pressure) may possibly be included.

Choosing an optimal spectral comparison and parameter to associate with pressure may depend on the microbubble 14 being used. It is expected that numerous types of ultrasound contrast agents being clinically qualified will, as the bubble references cited herein, display a good monotonic behavior of pressure versus a monitored acoustic parameter. The present invention is directed towards improved methods utilizing and presenting the results from such experimentally determined algorithms relating pressure and acoustic behavior. One algorithmic example that can be utilized in the present invention to relate resonant frequency to localized pressure can be expressed as follows:

$$f_0 = (1/2\pi)(3 \ y/p)^{1/2}(4 \ \pi/3 \ mR_m T)^{1/2}(P)^{5/6}$$

where y is the ratio of specific heat at constant pressure to specific heat at constant volume, p is density of ambient fluid, m is the mass of the gas, $R_m$ is the gas constant per gram, T is the absolute temperature of ambient fluid in Kelvins, and P is the ambient pressure. For harmonic imaging, an algorithmic expression for the frequency $f_{nd}$ is:

$$f_{nd} = (1/c)(2 \ nf_v \cos \theta)$$

where $n=\frac{1}{2},1,2,3\ldots$ (subharmonic, 1st, 2nd, 3rd harmonics), $f_t$ is the transmitting frequency, v is the velocity of the flowing fluid, θ is the angle between the transducers and the flow, and c is the sound velocity in the fluid.

It should be noted that the discussion of FIGS. 1A and 1B is focused on determining pressure changes from spectral changes. It will be obvious to one skilled in the art that it is possible to deduce or infer absolute pressure from a single spectra as opposed to a pressure change. For example, it is known that the above equation relates bubble resonant frequency to absolute pressure. It is also known that the reflective power of microparticles is related to their size (among other material parameters) in an absolute manner. In practice, encapsulated or filled bubbles are used where a closed-form parametric relationship may be determined experimentally. Further, the viscoelastic effects of polymeric bubbles may be taken into account. Thus it is possible to colorize blood pressure spatially in a manner not requiring comparison of two spectra taken at two points in time. It will also be apparent to those skilled in the art that this invention may be practiced using mixed bubble populations such as bubbles of two discrete sizes. This can make it easier to apply the algorithms since more information is available.

The shifting spectra resulting from the pressure changes undergone in the heart 10 can be depicted in relative terms, preferably in a colorized fashion, in a 2D or higher mapping. In accordance with the present invention, the relative shifting spectra or single spectra are used to colorize or otherwise graphically encode an image to provide a visually efficient representation of the pressure states experienced by the bubbles in the blood. A key contribution of this invention is that the information being mapped relates to pressure as determined using microparticles and is presented in at least two dimensions and may be presented in as many as four dimensions (including time). Flow may be separately determined using prior Doppler related techniques or any other known method. A 2D or higher mapping can then be displayed, as in prior Color Doppler techniques, independently or in conjunction with existing ultrasound modalities such as B-mode gray scale.

Figure 2A:
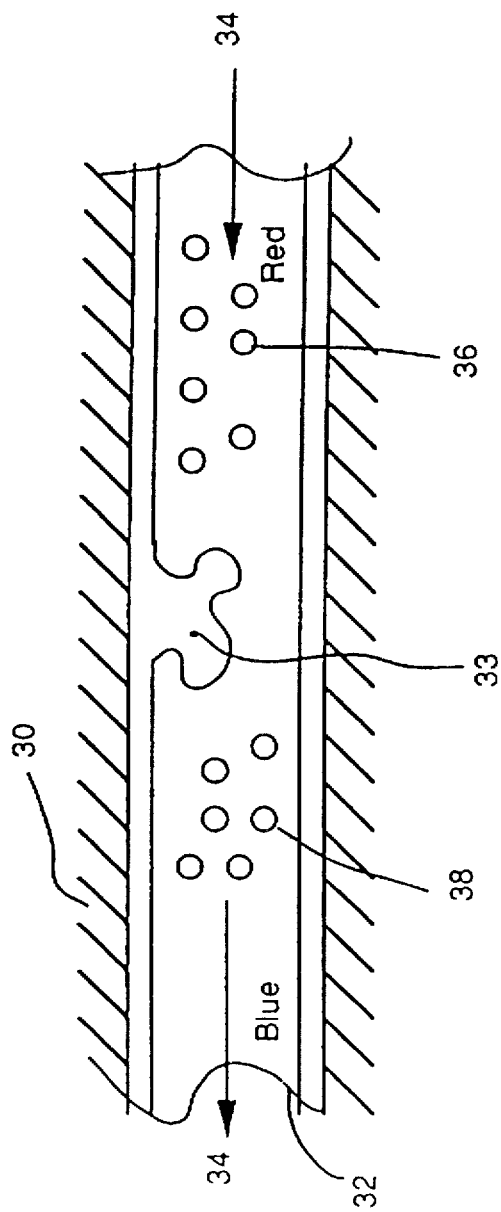
FIG. 2A shows a blood carrying-artery having an obstruction inside and its affect on the flowing blood and microbubble population.

FIG. 2A shows the utilization of the preceding principles to depict blood flow in a blood carrying-artery for ultrasound imaging. Bodily tissue 30 is shown surrounding a blood-carrying artery 32 containing a blood flow 34 flowing from right to left. Within blood flow 34, are microbubbles 36 and 38 suspended in and flowing with blood flow 34. A thrombus or obstruction 33 is shown attached to the upper interior surface of artery 32 where moving microbubbles 36 must flow around obstruction 33. Upstream of the obstruction 33, the microbubbles 36 experience a higher pressure than the microbubbles 38 on the downstream side of obstruction 33. In other words, the blockage restricts the flow and causes a localized blood pressure drop across obstruction 33, when flowing from right to left. Using the principles of the previous discussion, the pressure differential can be easily colorized using techniques similar to Color Doppler imaging. By way of example, the blood upstream of the obstruction 33 in the region of bubbles 36 may be graphically shown on the display screen as red in color, signifying higher pressure, whereas the blood flow downstream of obstruction 33 in the region of bubbles 38 could be depicted as blue representing lower relative pressure. Alternatively, it may be useful to utilize the intensity of a particular color, for example red, to depict pressures. The advantage of color representation of blood pressure is that obstructions can be quickly identified by color-shifted or color-affecting visual means. This eliminates the need to look specifically for a small obstruction. Thus it is only necessary to look for a change in color to signify pressure changes caused by obstructions, which is very efficient. Further, the present invention permits one to look for significant color (pressure) changes along a vessel as an indication of flow obstructions or impairments. Therefore, it becomes possible to pick out plaque deposits by noting the colorized pressure drops taking place in such an occluded vessel. For example, such a flow restriction causes a steeper pressure (color) gradient than normal increasing the likelihood of detection.

Figure 2C:
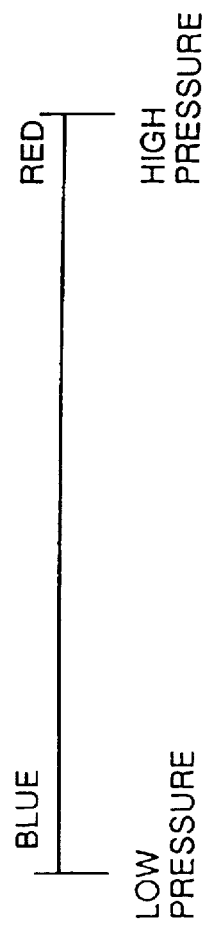
FIG. 2C schematically indicates a color scale which relates to the blood pressure in the artery.
Figure 2B:
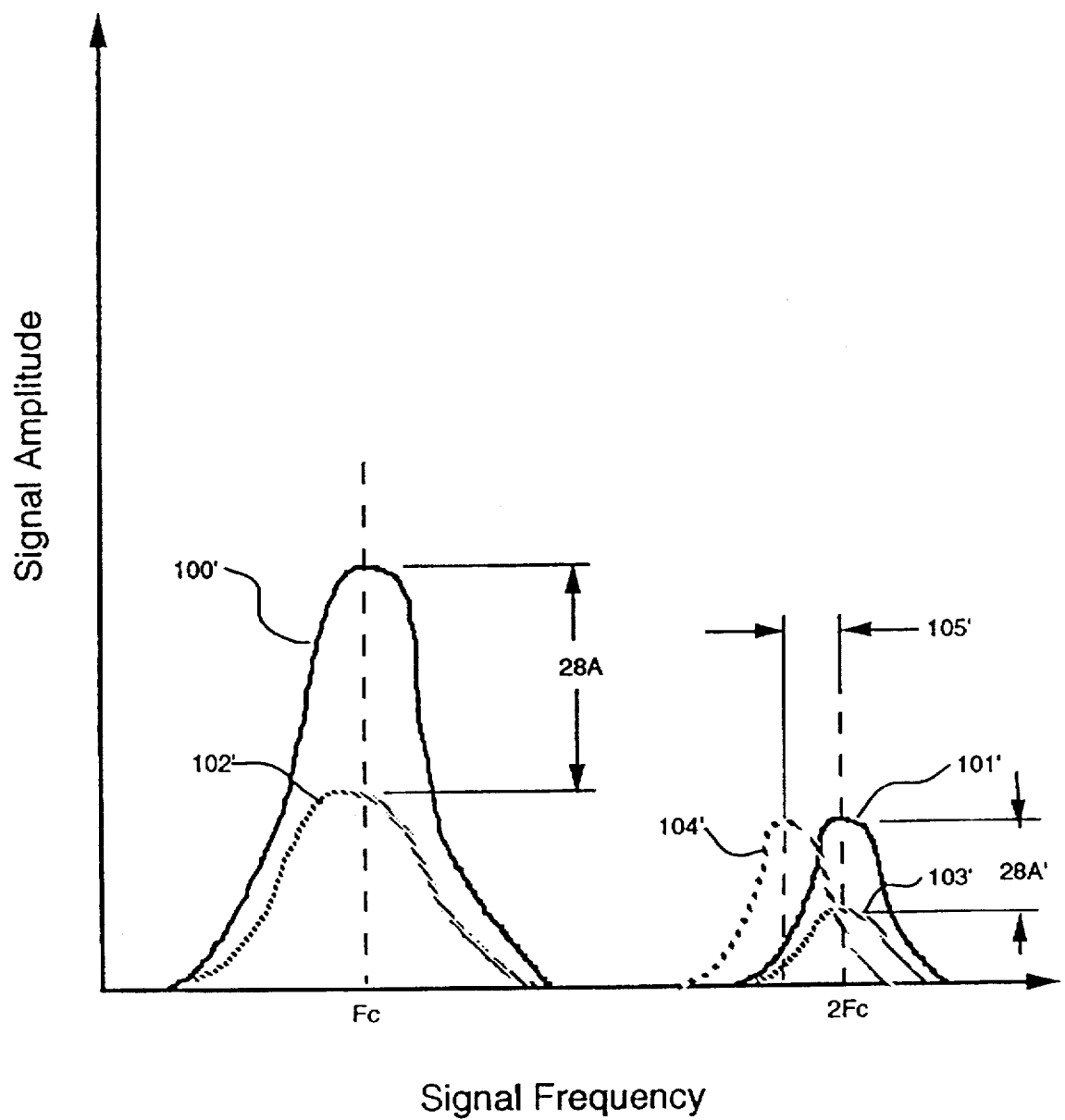
FIG. 2B shows a graph of the resulting acoustic spectra due to the pressure change in the artery caused by the obstruction.

FIG. 2B shows comparative spectral peaks in a manner similar to that of FIG. 1B. FIG. 2B shows peaks 100' and 101' are low pressure peaks but are associated with a low pressure measured from bubbles 38 of FIG. 2A. Peaks 102' and 103' are high pressure peaks but here are associated with a high pressure measured from bubbles 36. It should be recognized that for FIG. 1B the same spatial point in chamber 12 (FIG. 1) is sampled at both a low and high-pressure time in the heartbeat. In FIG. 2B, however, two spatial points are sampled at approximately the same time (i.e. upstream bubbles 36 and downstream bubbles 38 of FIG. 2A) as depicted in FIG. 2B. In this manner the instantaneous pressure delta across obstruction 33 is obtained.

In FIG. 2B (relative to FIG. 1B) the primed reference numbers indicate that similarly returned peaks will not likely be the same in terms of amplitudes etc. between heart 10 and artery 32. In particular, the pressure drop across obstruction 33 may be much larger than the pressure drop in chamber 12 over a heartbeat. Similarly to FIG. 1B, a frequency downshift 37' is seen in the harmonic signal consisting of peaks 27' at time t' and peak 35' at time $t_2$'. Further, it is also possible to monitor amplitude changes of 28A and 28A' or changes in frequency or phase.

As with heart 10, artery 32 may be visualized in dynamic real-time color wherein color may selectively represent at least one of flow, pressure or hemodynamic (hydraulic) work (all of which are included in the term "pressure parameter"). Artery 32, as blocked in part by obstruction 33, will be preferably depicted in color with this invention in a manner wherein everything upstream will have, for example, a red color and everything downstream a blue color.

FIG. 2C schematically indicates a color bar or color scale which relates the blood pressure in artery 32 (shown in FIG. 2A) to color. It should be obvious to one skilled in the art that, in addition to colorization, there are a number of other ways to relate a parameter such as pressure to a graphical image-wise mappable parameter such as color. By way of example, in a black and white scheme, one could have gray levels correspond to pressures or an image persistence (time to fade) relation to pressures. Another example is to display only the arterial pressurized blood in color and the surrounding tissue in B-mode. Accordingly, all variations of display modes for forming 2D or higher pressure parameter mappings are included in the spirit and scope of the present discussion. It may even be desirable to provide an audio output whose volume or tone is related to the instantaneous pressure at a point or at a particular sample volume. Included specifically herein are schemes wherein one may physically measure one or more "calibration" pressures in the body using secondary conventional means such as a cuff and pressure catheters etc. One may then be highly confident that the absolute pressures reported from the bubbles are properly calibrated.

A new form of information, derived in part from the pressure information discussed above, can now be computed and presented to the user. This new information is the amount of work being performed by or on an imaged organ. For example, the energy expended by the heart during a heartbeat cycle can be determined in a noninvasive and relatively simple straightforward manner. Basic fluid mechanics teaches that the product of pressure and flow (akin to force and displacement in mechanics) represents the energy or work related to that flow, whether it be the energy needed to pump the liquid or the power available from a liquid filling a cylinder and extending a cylinder rod to do useful work. If the pressure and/or flow is unsteady with time, the energy product may be mathematically integrated and thus derived. Therefore, a further novel contribution of the present invention is that by combining previously described mappable pressure means with existing or future (e.g. Doppler-related) flow measuring means, both pressure and flow information is available to directly calculate the work product.

Figure 3:
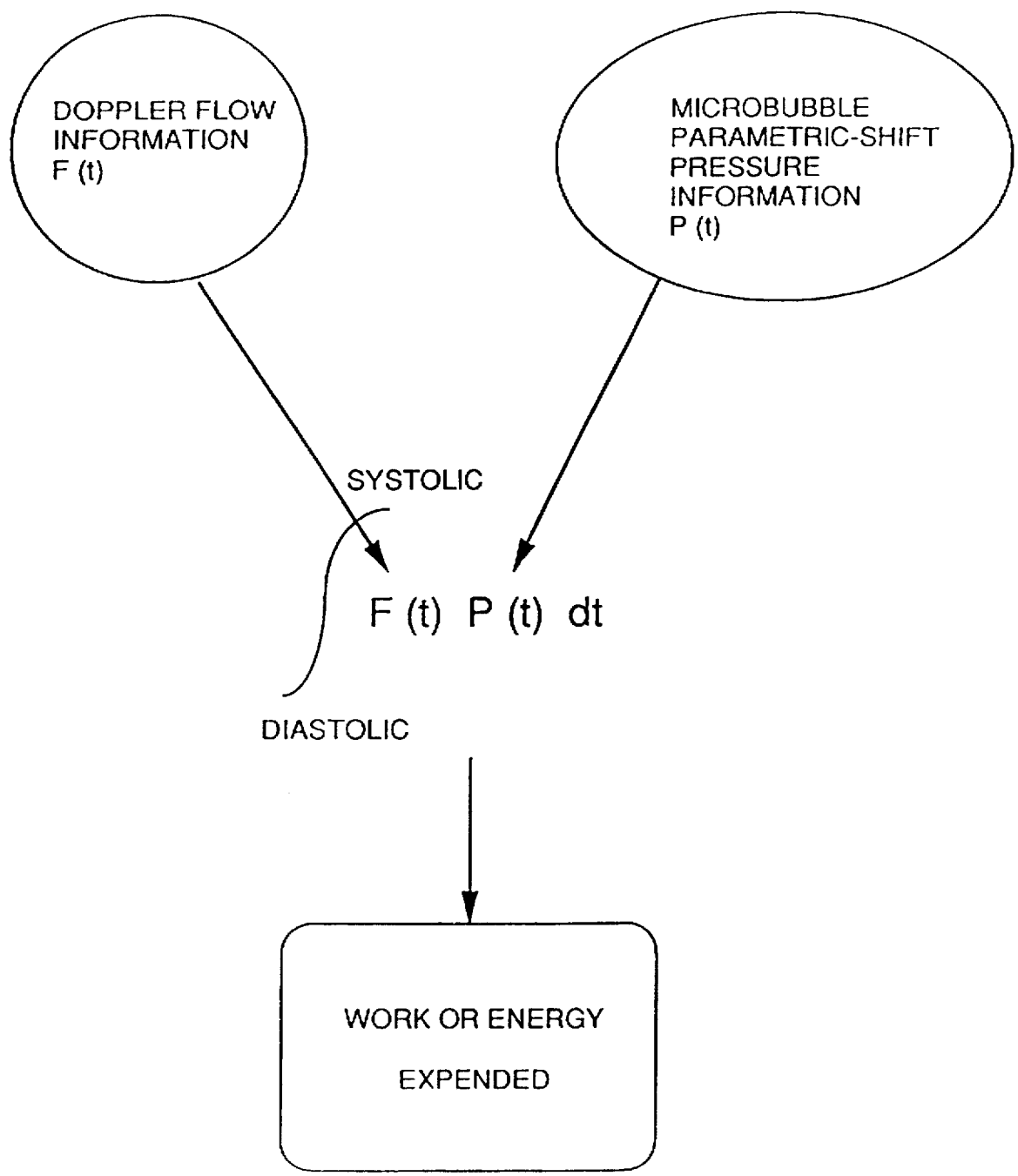
FIG. 3 shows the mathematical relationship of flow and pressure in the computation of work or total energy expended over a sample volume, in this case at a point.

FIG. 3 schematically shows a mathematical integration for the combination of Doppler flow information F(t) which is a function of time at a particular location and pressure P(t) which is also a function of time at that location. One may easily measure both of these parameters of pressure and flow using the described mappable pressure means of the present invention and existing Doppler flow means (color Doppler, color Doppler energy etc.) to derive an energy or work quantity, which may then be presented in a colorized form. For the heartbeat cycle there are two extreme pressures (diastolic and systolic) therefore an integration of the pressure x flow product over the time span represented by such a pressure cycle results in a work or energy quantity. Obviously, if the heart is imaged, one may do such an integration over an appropriate period of a heartbeat cycle and compute a quantity representative of the hydraulic work done by the heart during various portions of its pumping action. It should be recalled that such an integration may be spatially and temporally done over a spatial region or volumetric region of the organ or over the entire organ. The work or energy product may be calculated in real time, for example, and indicated numerically, graphically as by colorization, or in an audio tone. Such graphical depictions of work (instantaneous work output or time-averaged) may be a uniform color for a control volume such as the entire heart or may be for depictions of work for multiple subvolumes or subareas in which case, energy expended by location may be seen.

The energy spent by an organ such as the heart pumping blood, is consumed not only by creating blood flow in open arteries and veins but also in causing perfusion and cyclic motions of various infused organs and vasculature. It is therefore possible to use the means of this embodiment to measure negative work (or flow energy resistance) done by an organ or vasculature which is being pumped into. Resistance to incoming energy can be a useful indication of the perfusability or elasticity of the particular organ tissue or vasculature.

As an example of the above, if the intent is to ascertain the ability of an organs' vasculature to allow for self-perfusion, one would gather both pressure cycle P(t) and flow cycle F(t) data which automatically takes into account the normal dilation (i.e. cross-sectional variations) of the vasculature as the pressure changes. By way of example, an unhealthy nonflexible and rigid vasculature region would be unable to dilate effectively and would therefore maintain small diameters during the pressure cycle. Using the energy mapping feature of the first embodiment, one may map the energy spent in pumping and distorting such a region. One would be concerned if either there is insufficient flow given an adequate local pressure cycle or if there is an inadequate local pressure cycle.

Figure 4A:
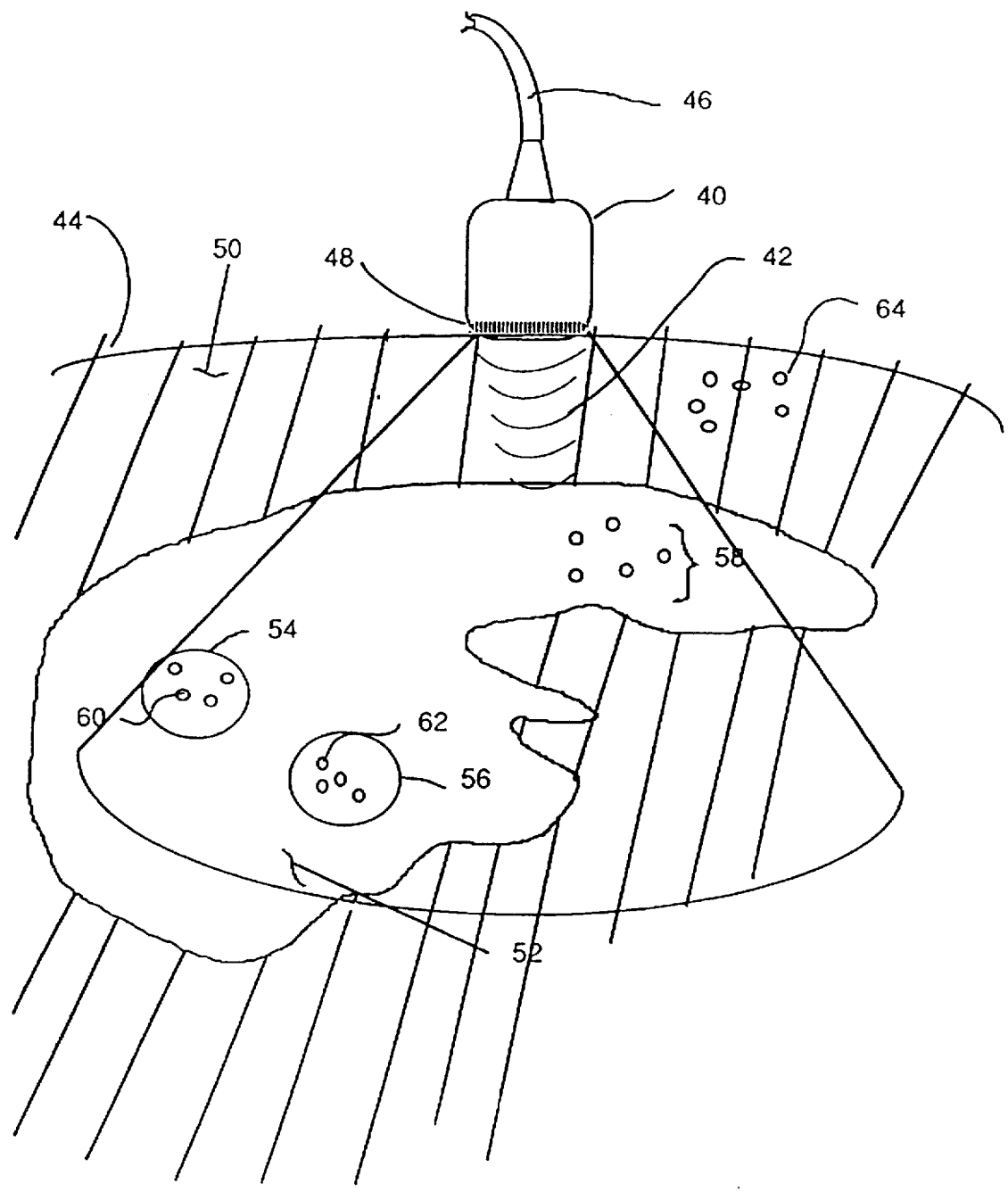
FIG. 4A shows a microbubble population perfused in both healthy and tumorous tissues in a liver which is imaged with ultrasound waves.

Referring now to FIG. 4A, a variation of the first embodiment showing a living body with a liver 52 being imaged by imaging transducer 40 through the body surface 44 is shown. Of note are two tissue regions within liver 52. Region 56 depicts a healthy tissue region whereas region 54 depicts a tumorous tissue region or some other pathogenic liver tissue, growth or deposit. Microbubbles are shown situated in liver 52 as bubbles 60 in tumor tissue 54, bubbles 62 in adjacent healthy liver tissue 56, bubbles 58 shown in remote healthy liver tissue, and bubbles 64 shown in tissue outside of the liver 52. Bubbles may be distributed by any means such as by catheter infusion or syringe injection. The imaging transducer 40 is shown imaging at least the region of the liver containing tumor and healthy areas 54 and 56 respectively with ultrasound waves of the type 42. The returned ultrasound waves resulting from ingoing waves 42 are converted into electrical signals that are transmitted through cable 46 back to a signal processor (not shown), where among other things, the signals are filtered and amplified to form an image.

An inventive aspect herein is the realization that tumors and other pathogenic tissues frequently have different mechanical and/or perfusive properties as compared with healthy tissue. Accordingly, microbubbles 60 situated in a pathogenic region 54 as opposed to a healthy region 56 will locally experience a different pressure waveform (as indicated by the bubble acoustic signature changing with changing blood pressure) induced by the remote pumping heart. The waveform difference may, for example, occur because the tumor is hard and nodular and of low perfusability. In this case microbubbles inside such a tumor would be "shielded" from the full pressure cycle relative to those in the softer more perfusive healthy adjacent tissue. Since microbubbles are capable of monitoring pressure in both a temporal and spatial fashion, it is possible to collect images of the liver and note that unhealthy regions may be differently colorized or otherwise graphically presented. It should be noted that this "shielding" may show up as one of an amplitude drop, a phase delay, or a resonance frequency change in the tumor bubble pressure waveform.

Figure 4B:
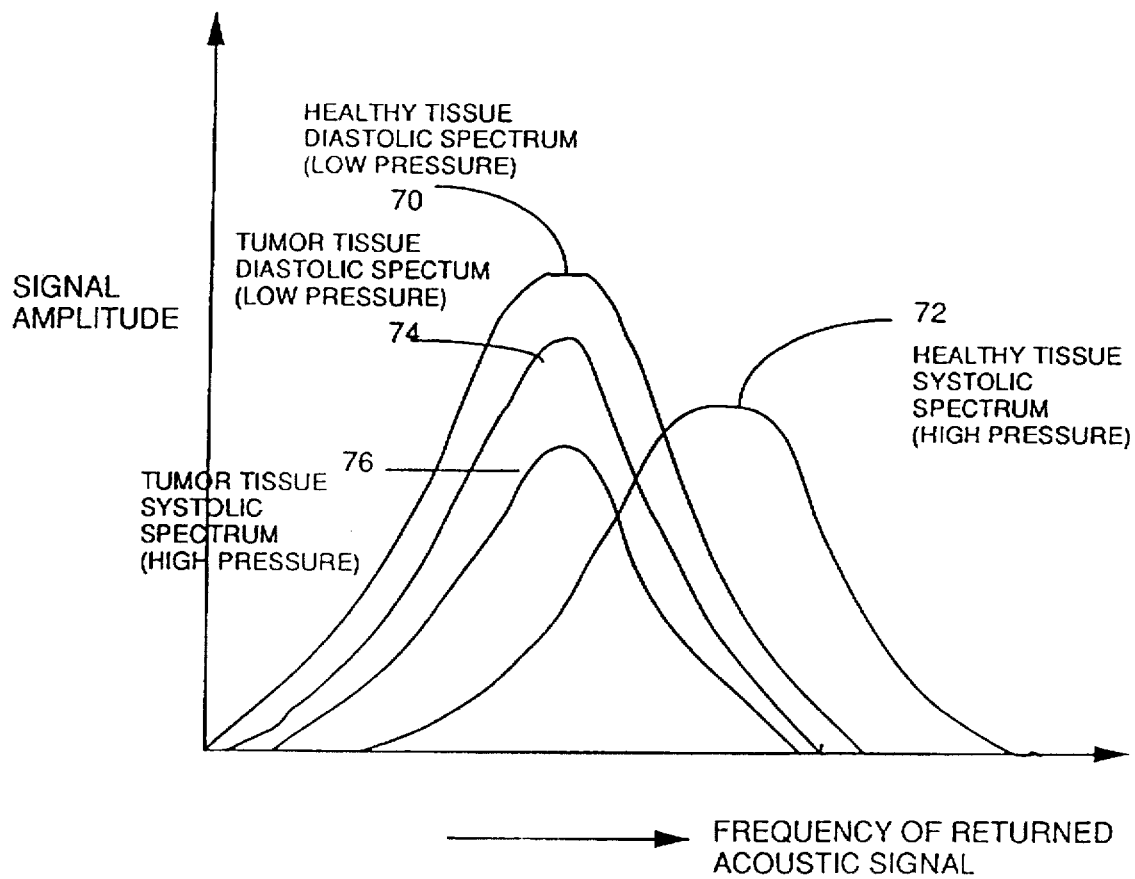
FIG. 4B is a graph of acoustic signals of the healthy and tumor tissue in FIG. 4A.

FIG. 4B is a comparison of waveforms generated from the arrangement in FIG. 4A. FIG. 4B depicts the possible effects on the primary peak only (no harmonics shown). The diastolic and systolic returned spectra is shown for both the tumor region 54 and the adjacent healthy region 56. The original incident spectra are not shown; only returned spectra are shown. It should be pointed out that healthy tissue 56 returned-spectra at the low and high local blood pressure time points are indicated by spectra 70 and 72 respectively. The low pressure curve 70 is lower in frequency and higher in amplitude by significant margins relative to curve 72. Previously shown was the general case wherein both amplitude and frequency shifts are seen. The amplitude drop in a given type of tissue (i.e. 54 or 56 in FIG. 4B) is related to the microbubble diameter change between high and low pressure. This diameter change causes the aforementioned changes in reflected amplitude. The frequency shifts shown might, for example, be related to resonance interactions or the sapping of energy into harmonics (not shown) as a function of pressure. One or more such monotonic relationships are used to ascertain an effective pressure of the microbubbles in the various locations versus time.

Further, in FIG. 4B there are two corresponding spectra for tumor tissue 54 region in FIG. 4A. Let us assume, for example, that tumor tissue 54 is hard and poorly perfused. In such a case, microbubbles inside tumor 54 would be shielded from the full pressure swing of the blood because the tumor is relatively incompressible and relatively impermeable when compared to healthy tissue. Thus we have spectra 74 and 76 corresponding to the diastolic and systolic cycles of the heartbeat, as shown in FIG. 4B. It can readily be seen that both the center frequency difference and amplitude difference between the high pressure curve 76 and low pressure curve 74 (both tumor tissue) are smaller than the corresponding differences between curves 72 and 70 (both healthy tissue). This is expected since the change in bubble size due to pressure is less dramatic because of the shielding effect described. Parameters relating to one or both of these differences between the two tissue types may be graphically displayed on an ultrasound image in colorized or other form.

The above embodiment is directed to variations on a passive system wherein bubble acoustics are affected by localized pressure resulting in a unique graphical signature. By passive it is meant that the imposed pressure differences were due to the body itself (e.g. heartbeat, natural organ motion, patient action etc.). Thus it has been shown how to passively monitor and display pressure, pumping work (or resistance to flow), and assess tissue health. Again it should be noted that the spectral characteristic changes used to create the graphical representation may be one, or many, and may be related to a returned reflected ingoing waveform or to some change(s) in a harmonic(s) returned due to the ingoing waveform. It should also be noted that, although center frequency changes and peak amplitude changes are illustrated herein as examples of characteristics of the acoustic spectra that can be used, other spectral characteristics can also be used to carry out the invention. For example, the spectra may be highly non-gaussian, in which case, the "center frequency" may not be symmetrically located, or the amplitude changes monitored may not necessarily be at a fixed point of maximum amplitude or even maximum amplitudes. Many different bubble spectral characteristics can be utilized to derive multi-dimensional displays or maps of graphical pressure representations, energy or work representations, or tissue health representations. For example, the integrated area of a spectrum is another possible parameter that may be used for the comparison of waveforms.

In a second embodiment of the present invention, an improved method for the detection of tumors based on the physics of microbubbles is described. Conceptually the idea is similar to that of the first embodiment, however, a notable difference is that the imposed probing pressure change is due to an externally applied action (e.g. by a doctor or sonographer) as opposed to natural or unaided occurrences such as a heartbeat cycle.

Figure 5A:
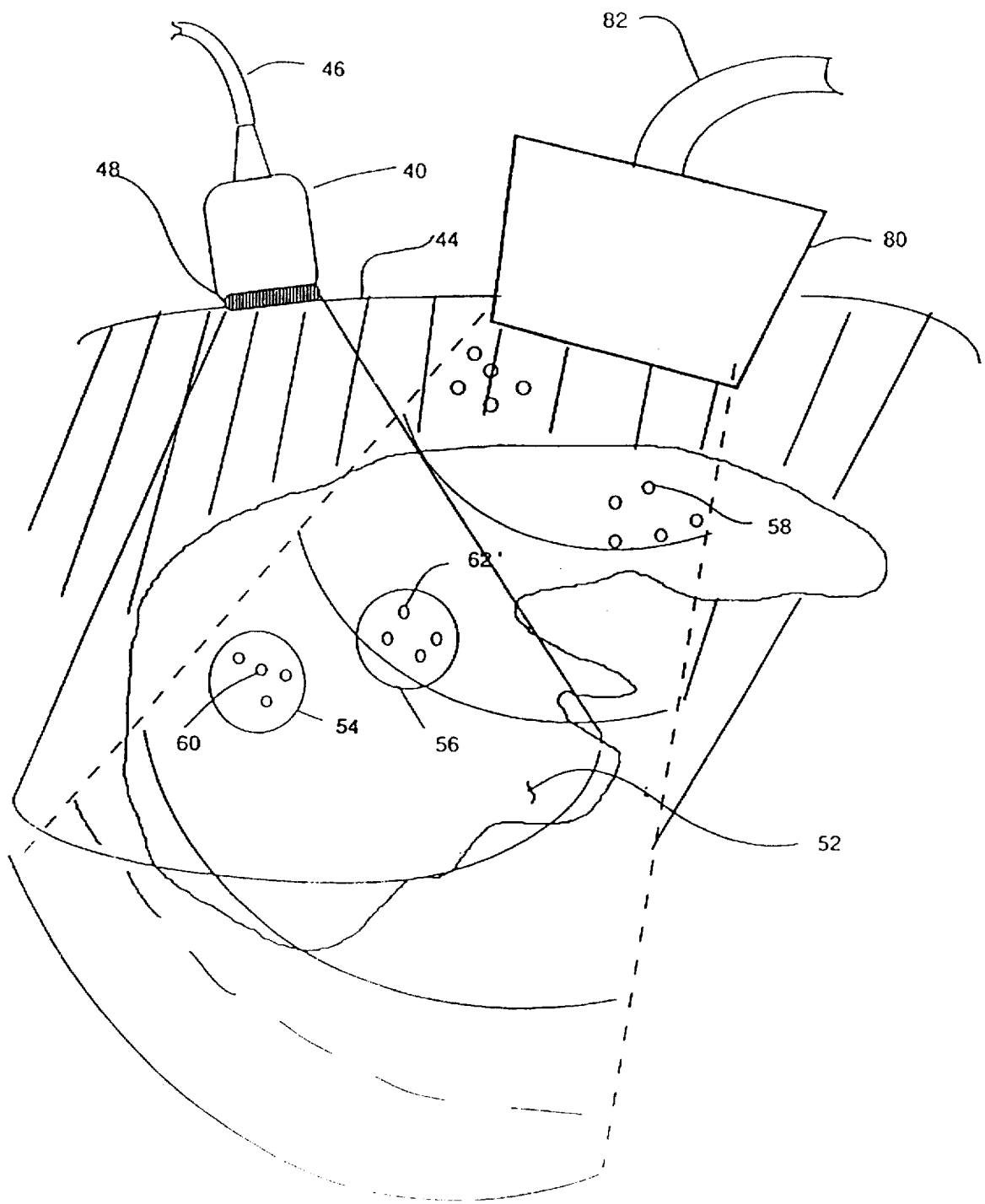
FIG. 5A shows the arrangement of FIG. 4A where an additional probing transducer is added to impose compression waves to the healthy and tumor tissue.

Referring now to FIG. 5A, a similar imaging transducer/ liver arrangement as in FIG. 4A is shown with the exception that there is a probing transducer or device 80 introduced, connected to a cable 82. In FIG. 5A, transducer 80 is used to impose a remote external cyclic (or static) probing-pressure on liver regions 54 and 56. Transducer 80 may be a separate device from the imaging transducer so that it is possible to have it impinge significant pressure pulses (compressional and tensional) of magnitude and phase quite different from any natural pressure cycle or anything deliverable from the imaging transducer. Specifically, transducer 80 may impose a low frequency vibration of a few tens of hertz to a few hundred hertz having a peak pressure amplitude or amplitude swing possibly much greater than that imposed by a heartbeat, for example. Probing transducer 80 may also be synchronized with imaging transducer 40 such that images are gathered by imaging transducer 40 only at the extreme low and high pressure times imposed by probe 80 or at other relative time points. In this manner, the microbubbles 60' and 62' in tumor tissue 54 and healthy tissue 56 respectively will demonstrate different reactions (in terms of amplitude, phase, and/or frequency shifting) in their high pressure and low pressure behavior as compared to healthy tissue. In FIG. 5A, however, transducer 80 provides the luxury of utilizing much larger imposed pressure swings of frequencies both slower and faster than what might occur naturally. It is expected that the most useful range of probing frequencies delivered by probe 80 would be from 0 Hz (static load) to 400 Hz.

For a saturated body having different permeabilities or flow resistance in different regions, the application of a macroscopic pressure-pulse will result in the various regions adapting to the pressure pulse (trying to equilibrate the local pressure with the instantaneous imposed compression/ rarefaction) via flow or deformation with differing time constants. Since it is possible to vary the frequency of probing excitation transducer 80, it can be swept over a broad range of frequencies to discover the frequencies at which pressure equalization takes place in a certain time. By way of example, a highly perfused and permeable tissue will rapidly equilibrate its local pressure as opposed to a poorly perfused and low permeability tissue. Thus, by sweeping the frequency of the probing transducer 80 from a range of approximately 0 Hz to several hundred Hz, it is possible to determine the hydraulic relaxation time of the various tissues and map and present a parameter directly related to their perfusability. It is to be emphasized that the perfusing equilibrating liquid may be any bodily fluid.

Figure 5B:
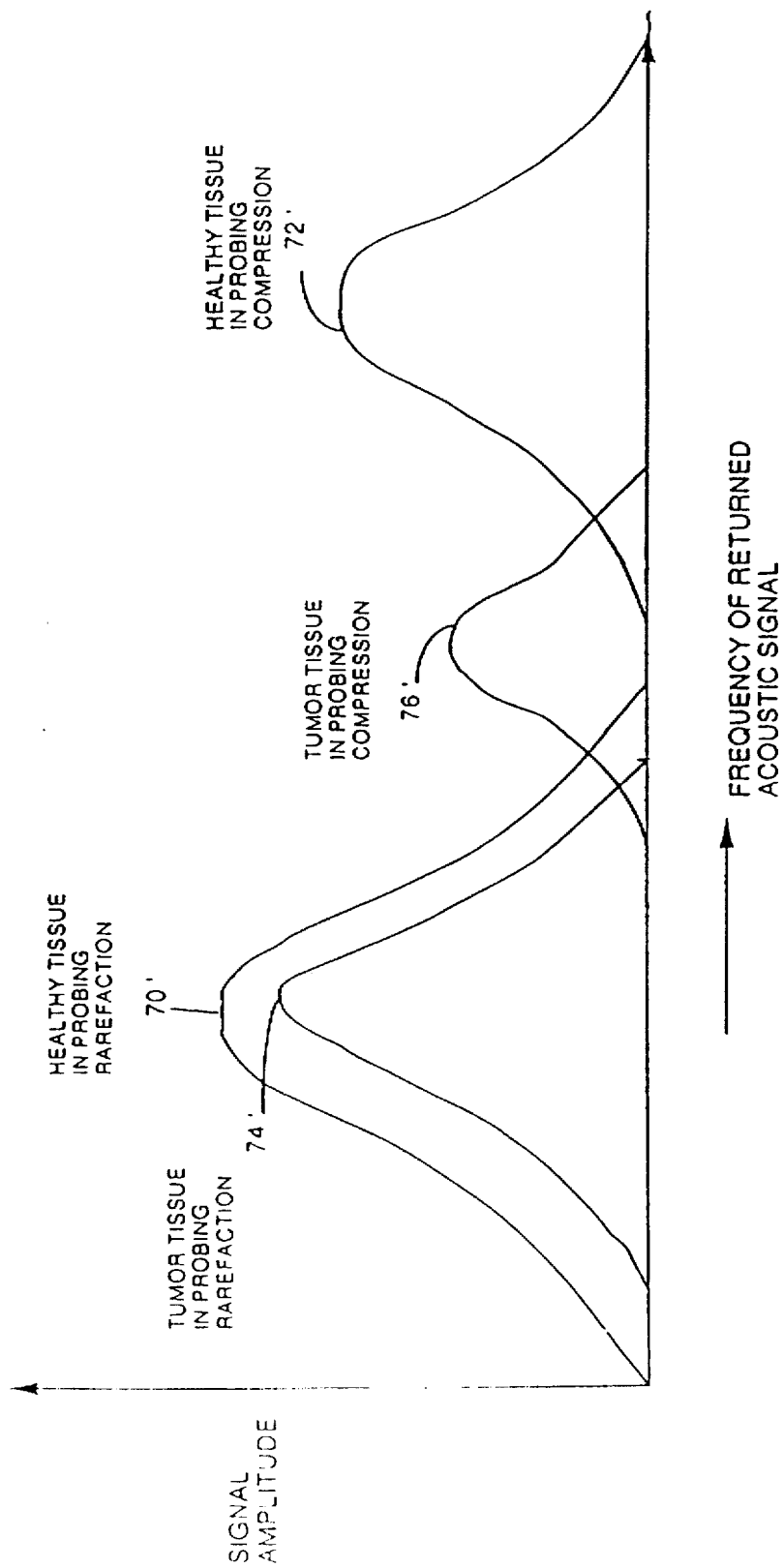
FIG. 5B is a graph of acoustic signals of the healthy and tumorous tissue in FIG. 5A.

FIG. 5B is a graph of the changing acoustic response due to the application of the probing transducer in FIG. 5A. Assuming a relatively large amplitude pressure vibration cycle is applied by transducer 80, it is expected that differences in the acoustic signatures of bubbles in healthy tissues versus in tumorous tissues will be more dramatically accentuated. As shown by comparison to FIG. 4B, FIG. 5B indicates that, for the larger externally applied pressure waves of device 80, there are larger differences in the amplitude and frequency deltas (if any) or differences between the tissue types for high pressure vs. low pressure spectra 70', 72', 74' and 76'. In other words, since the pressure change that probe 80 can apply to the tissue may be much larger than the pressure change caused by the heartbeat, one expects correspondingly larger signal amplitude shifts and frequency shifts.

A low frequency excitation or probing wave from device 80 having a 0 hertz frequency of static compressional or tensional load may be simulated by a doctor's hand or a suction cup pulled while applied to the skin. This is akin to remote palpitation since the doctor is "feeling" the response with the changing acoustic bubble signature. The resulting acoustic signals from the various tissue regions may be dynamically colorized or otherwise graphically displayed (i.e. mapped in at least 2 dimensions), as discussed in the previous embodiment, for a more visually efficient method of detecting tumors. It should be noted that both amplitude and frequency shifts are shown in FIG. 5B. Possible phase shifts are not shown or an amplitude shift may be present alone.

An advantage of the present embodiment is that detection is not dependent upon the size of the tumor in that it can be effective as long as the microbubbles are able to penetrate into the tumor regardless of size. Since microbubbles are typically in the range of 0.5 to 2 microns, small tumor sizes e.g., 1 mm tumors, can be resolved using the method of the present embodiment. It will be appreciated by those skilled in the art that microbubbles which surround a stiff tumor may also have the pressure waveforms they experience affected in amplitude or phase. This is particularly the case for microbubbles which are physically obscured from an incoming low frequency palpation probing wave because the bubbles are on the far side of such a tumor.

Selection of contrast agent should be tailored to the effective presentation of the fluid pressure parameter being mapped, the acoustic spectral characteristics that will conveniently be detected as a result of the returned echo from the agent, and the algorithm relating the spectral characteristic to the pressure parameter, for example.

In the embodiments described above, any microbubbles of the type that are acoustically responsive in a predictable manner to pressure may be used. By way of example, gas filled polymer bubbles and solid gel-like bubbles are known to have predictable variable acoustic signatures and thus work well with the present invention. Specific examples include "Albunex" manufactured by Molecular Biosystems Inc., San Diego, Calif. or "Levovist", part number SHU508, manufactured by Schering AG, Berlin, Germany. Further, there are various methods of introducing microbubbles into the body such as orally or intravenously that work correspondingly well with the present invention. Similarly, the precise placement of the imaging transducer 40 and probing transducer 80 are not limited to the types and position as shown in the Figures. For example, imaging transducer 40 may be of either the external type such as transthoracic, intracavity type (e.g. endocavity endorectal or endovaginal), or intraluminal type (e.g. catheter based). Probing transducer 80 may be located externally or internally to the body or perhaps even physically integrated with the imaging transducer 40 itself.

It should also be pointed out that the pressure probing effect of device 80 may alternatively be provided by fluid pressure, pneumatic pressure or body acceleration/deceleration. The fluid or pneumatic pressurization probing means might, for example, be introduced directly into a questionable organ via a saline-injecting syringe for example. Also, multiple microbubble populations may be introduced into the body where each population may have different spectral characteristics. The combined spectrum may be used in the described embodiments to determine pressure and the presence of abnormal growths. Further, the utility of the present invention is not limited to analysis of the heart but can be used on any organ or tissue inside the body where fluid pressure mapping, flow-work or tumor detection is desired. By way of example, microbubbles suspended in blood, urine, brain-case fluid, or placental fluid may be used for mapping and presenting fluid pressure and/or detecting tumors in the liver, kidneys, brain etc., and fetus as well.

Figure 6:
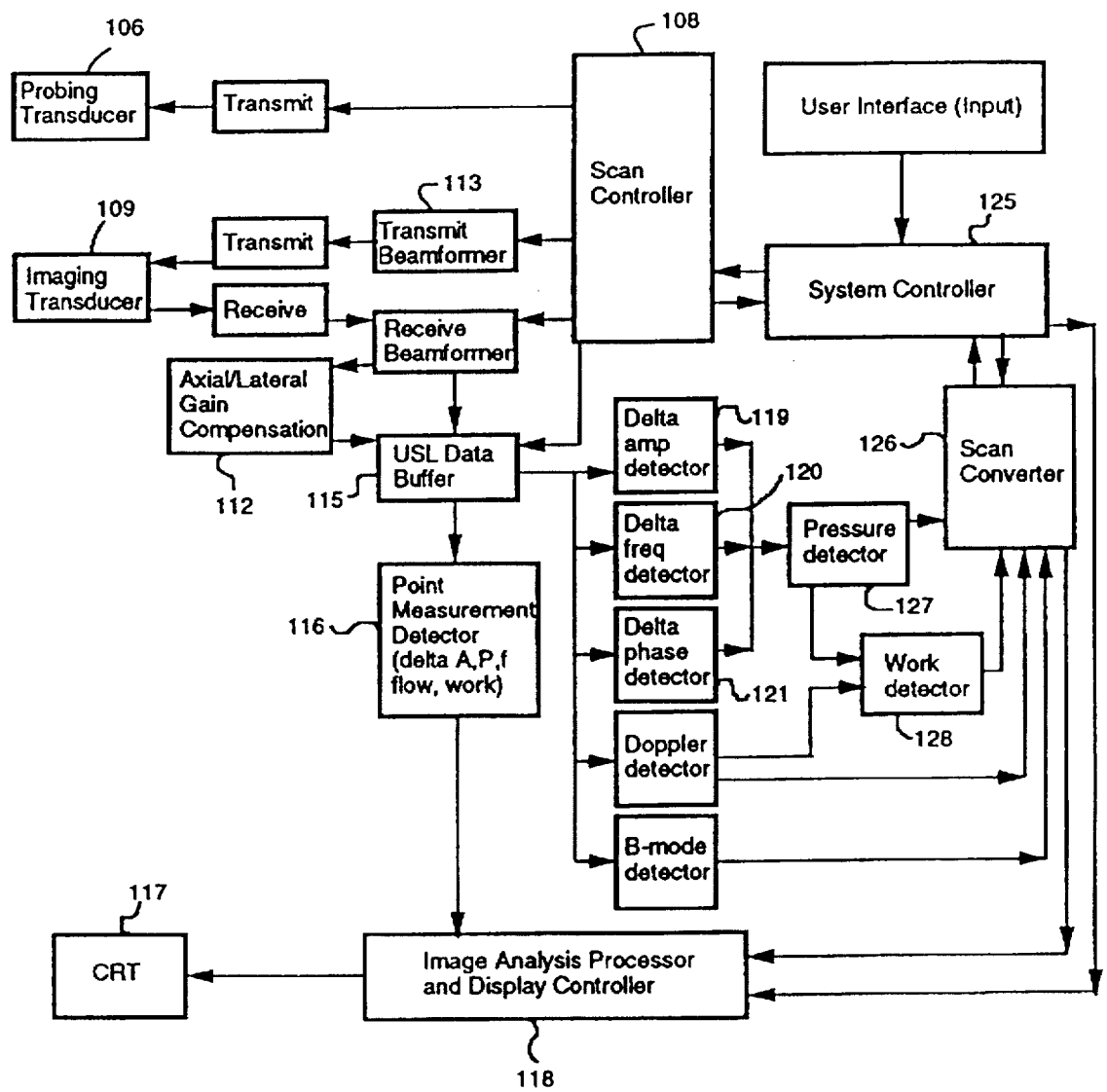
FIG. 6 is a schematic block diagram of an ultrasound system in accordance with the present invention.

Referring now to FIG. 6, a block diagram of a typical ultrasound system used with the present invention is shown. An ultrasound line (USL) data buffer 115 is used to store multiple frames of USL data received from an imaging transducer 109. A scan controller 108 is coupled to USL 115 which controls the sequence and timing for USL transmission and reception of data. The USLs may be acquired sequentially across each frame, or may be interleaved in any one of a multiplicity of interleave patterns including multiple firings of a single USL before firing the next USL. Delta amplitude detector 119, delta frequency detector 120, and delta phase detector 121 receive and process data from the USL data buffer 115 as needed by the scan controller 108. A point measurement detector 116 is coupled to and receives data from the USL data buffer 115 in which data from a single or small number of range gates which in turn come from a single or small number of USLs. This permits single, multiple, and differential point measurements to be sent to an Image Analysis Processor and Display Controller 118 for display to CRT 117. A scan converter 126 is coupled to system controller 125, pressure detector 127, and work detector 128. The scan converter 126 includes processing capabilities for B-mode, color Doppler, and spectral PW Doppler images. The point data and scan converted data is then sent to the Image Analysis Processor/Display Controller 118 which prepares and displays all images and graphics on CRT 117.

The Image Analysis Processor/Display Controller 118 is coupled to and receives data from the Point Measurement Detector 116, Scan Converter 126 and System Controller 125. Display Controller 118 is capable of displaying ultrasound B-mode (gray scale), color Doppler, colorized image pressure, colorized work (flow energy), and colorized tissue properties. In addition, all of the previous modes may be displayed as an M-mode strip, PW Doppler strip, and a region of interest (ROI) bordering. A waveform display of the ROI is calculated from data and Point Measurement Data as function of time and temporal or spatial integration for the items in the ROI. The point measurement data can come from either the Point Measurement Detector 116 or the scan converted image from Scan Converter 126.

The returned energy from the microbubbles will typically be received at both the fundamental transmission frequency as well as at the various super and sub-harmonics. Shifts in the amplitude in the acoustic spectra of the harmonics relative to the fundamental frequency are determined by various filtering stages in the ultrasound system which, in turn, are effected by the local fluid pressure. Probing transducer 106 is controlled by Scan Controller 108 (for the second embodiment) to provide timely palpitating action to the examination area. Imaging transducer 109, which transmits and receives acoustic energy to and from the examination area, is also coupled to Scan Controller 108 through transmit beamformer 113. A 2D relative strength measurement is performed by comparing the various harmonic images to the fundamental image through the delta amplitude, frequency, and phase detectors 119, 120, and 121 respectively.

An Axial/Lateral Gain Compensation stage 112 is added to compensate for the spatial intensity variations due to beamformation and scan format selections, filtering etc. It insures that the variations depicted are due only to microbubble scattering and associated local pressure variations. When relative pressure changes are small, they may be amplified or enhanced by employing a technique of combining two images using a 2-D lookup table and a 2-D filter. Such a technique is disclosed in U.S. Pat. No. 5,479,926 issued to Ustuner et al. entitled: Imaging System Display Processor granted on Jan. 2, 1996 which is incorporated by reference herein in its entirety. The output image of this image display processor is an arbitrarily weighted combination of an image and a filtered version of the same image. The weighting or mapping is accomplished through suitable numeric values stored in the 2-D lookup table. This can then be used to extract local pressure changes and enhance their subsequent appearance on CRT 117 in gray scale (B-mode) and color. The technique can also be used with two images wherein each image is distinct, i.e., one is not a filtered version of the other. In this case the images may be generated with different beamforming parameters, or come from different modes such as B/F or may simply come from two images sampled at different time intervals. The imaging display processor could be incorporated within the Image Analysis Processor and Display Controller 118.

It should be noted that the present invention may be practiced with current or future ultrasound technology that, for example, uses multiple beams and low-flow detection modalities. By way of example, color Doppler energy related means typically used in low-flow detection may be utilized to measure bubble integrated backscatter as a function of pressure in time and space.

Although the invention has been described in some respects with reference to specified preferred embodiments thereof, variations and modifications will become apparent to those skilled in the art. It is therefore, the intention that the following claims not be given a restrictive interpretation but should be viewed to encompass variations and modifications that are derived from the inventive subject matter disclosed.

What is claimed is:

1. A method of mapping and presenting a fluid pressure parameter in a living body comprising the steps of:
   introducing microbubbles into said body;
   applying ultrasound waves to the body wherein returned waves from the microbubbles contribute to the formation of an acoustic spectrum associated with the microbubbles;
   determining a fluid pressure parameter in response to at least one characteristic of the acoustic spectrum; and
   mapping the fluid pressure parameter in at least two dimensions.

2. A method according to claim 1 wherein the microbubbles are introduced into the body such that they are suspended in a natural body fluid.

3. A method according to claim 2 wherein said fluid is one of blood, urine, brain-case fluid, placental fluid, and spinal fluid.

4. A method according to claim 1 wherein the fluid pressure parameter is a function of blood pressure.

5. A method according to claim 1 wherein the presented pressure parameter is colorized in accordance with a color scale relating to pressure.

6. A method according to claim 5 wherein said colorization relates to the pressure in a monotonic manner.

7. A method according to claim 1 wherein said characteristic includes any one of a phase, an amplitude, and a frequency.

8. A method according to claim 1 wherein the mapping step further comprises mapping temporal changes in at least one characteristic of the spectrum.

9. A method according to claim 8 wherein the mapping is accomplished by color coding.

10. A method according to claim 1 wherein the mapping step further comprises mapping spatial changes in at least one characteristic of the spectrum.

11. A method according to claim 1 further comprising the steps of computing the energy output of the heart from said pressure parameter in association with flow information obtained using Doppler techniques and displaying a colorized representation of the energy.

12. A method according to claim 1 comprising in the mapping step, representing dynamically changing pressure in the heart and associated regions during a heartbeat cycle.

13. A method according to claim 1 wherein said microbubbles further provide contrast enhancement for improved B-mode and Doppler related images.

14. A method according to claim 1 wherein said presented pressure information is displayed in association with any one of B-mode and Doppler-related ultrasound images.

15. A method according to claim 1 wherein the microbubbles are introduced into the body by one of oral and intravenous methodologies, whereby said microbubbles are comprised, at least in part, of any one of biocompatible gas, gel, and polymer material.

16. A method according to claim 1 wherein at least one of the mean pressure, maximum pressure, minimum pressure, and pressure swing is measured, recorded, and presented for at least one spatial point.

17. A method according to claim 16 wherein said colorization comprises a color scale relating color to at least one pressure-related parameter.

18. A method according to claim 1 wherein the returned waves are at least one of reflected waves or harmonically excited waves.

19. A method according to claim 1 wherein at least one pressure measurement is taken from the body using conventional means, and is used to calibrate pressure readings derived from said bubbles.

20. A method according to claim 1 wherein the characteristic includes any one of: relative amplitudes of two or more harmonic peaks; relative amplitudes of at least one harmonic peak; and a characteristic in the primary spectrum.

21. A method according to claim 1 wherein the microbubbles introduced into the body are comprised of least two microbubble population types, each microbubble type having a distinct acoustic spectrum that contributes to combined spectra used to compute pressure within said body, said pressure being mapped, recorded, or presented in at least two dimensions.

22. A method of mapping and graphically presenting in at least two dimensions the hydraulic work performed by or on a bodily organ or vasculature comprising the steps of:
   introducing microbubbles into a living body such that the microbubbles enter the organ or vasculature;
   applying ultrasound waves to the body wherein returned waves from the microbubbles contribute to the formation of an acoustic spectrum associated with the microbubbles; and
   determining a pressure parameter in response to at least one characteristic of the acoustic spectrum;
   wherein said hydraulic work is computed from, at least in part, a product of pressure parameter and flow information obtained using Doppler-related techniques.

23. A method according to claim 22 wherein the bodily organ is a heart.

24. A method according to claim 22 wherein the bodily organ is a liver.

25. A method according to claim 22 wherein the bodily organ is a kidney.

26. A method according to claim 22 wherein the work is recorded on a recordable media.

27. A method according to claim 22 wherein the work performed is colorized in at least two dimensions that depicts areas of relatively higher work output as represented in red and areas of relatively low work output represented in blue and intermediate work output is represented by gradations in between red and blue.

28. A method according to claim 22 wherein the hydraulic work is at least one of presented, recorded and displayed in association with any one of B-mode and Doppler-mode ultrasound images.

29. A method according to claim 22 wherein a representation of work is presented and depicted in a static three dimensional colorized fashion.

30. A method according to claim 22 wherein a representation of work is presented and depicted in a dynamic three dimensional colorized fashion.

31. A method according to 22 wherein microbubble behavior is observed in a time period of a blood pressure cycle.

32. A method according to claim 22 wherein the condition of circulatory system is assessed from the work output of the heart.

33. A method according to claim 22 wherein the microbubbles introduced into the body are comprised of least two microbubble population types, each microbubble type having a distinct acoustic spectrum that contributes to combined spectra used to compute pressure within said body, said pressure being mapped, recorded, or presented in at least two dimensions.

34. A method of assessing the health of bodily organs, vasculature, or bodily tissue comprising the steps of:
   introducing microbubbles into the body;
   applying high frequency sound waves to the region to be examined thereby causing an acoustic spectrum to be returned from the microbubbles;
   determining pressure changes in response to at least one characteristic of the returned acoustic spectrum of microbubbles infused in said organs and tissue, wherein differences in the spectral characteristics of the microbubbles are used to assess the presence of abnormalities in the examined region and are displayed in at least a two dimensional mapping for presentation to the user.

35. A method according to 34 wherein the characteristics are comprised of changes of at least one of: a microbubble resonant frequency; a microbubble harmonic frequency; reflective power; degree of contrast; and amplitude and phase angle.

36. A method according to 34 wherein the presence of abnormalities is presented in a colorized fashion wherein the state of health is depicted as: areas that contain no abnormalities are represented in blue; areas containing abnormalities are represented in red; and areas containing varying degrees of abnormalities are represented as a gradation between red and blue in accordance to the degree.

37. A method according to 34 wherein the mapped representation of the health of the organ, vasculature, or tissue is presented in conjunction with other ultrasound imaging modalities.

38. A method according to 34 wherein spectral characteristic is observed in a time period during the influence of an external probing low frequency wave applied to the region being examined.

39. A method according to 34 wherein spectral characteristic is observed in a time period after the influence of an external low frequency wave applied to the region being examined.

40. A method of detecting one of tumors, lesions, or abnormal growths in a human body comprising the steps of:
   introducing microbubbles into a region of the body to be examined, wherein said microbubbles infuse into both healthy tissue and tumor tissue;
   applying high frequency sound waves to the region to be examined thereby causing an acoustic spectrum to be returned from the microbubbles;
   applying an external low frequency pressure wave to the region to be examined;
   monitoring at least one characteristic of the acoustic spectrum of said microbubbles in response to the applied external compressional wave; and
   ascertaining the presence of tumors, lesions, or abnormal growths from changes in the spectral characteristics between the healthy tissue and tumor tissue.

41. A method of detecting tumors according to claim 40 wherein the high frequency sound waves are applied through an ultrasound imaging transducer probe.

42. A method of detecting tumors according to claim 40 wherein the external pressure wave is a compressional wave or wave train.

43. A method of detecting tumors according to claim 40 wherein the external pressure wave is a tensional wave or wave train.

44. A method of detecting tumors according to claim 42 wherein the external compressional wave is applied through an external transducer probe.

45. A method of detecting tumors according to claim 42 wherein the external compressional wave is created by an examiner's hand.

46. A method of detecting tumors according to claim 40 wherein pressure experienced by the microbubbles is computed and presented to the examiner to assess the properties of the growth.

47. A method of detecting tumors according to claim 40 wherein the changes in acoustic spectral characteristics are represented and displayed in a colorized fashion.

48. A method of detecting tumors according to claim 47 wherein the colorized display is depicted in conjunction with ultrasound B-mode and Doppler images.

49. A method according to 40 wherein the probing low frequency wave operates in cooperation with ultrasound imaging such that the images are sampled at specific times during or related to the probing excitation cycle.

50. A method according to 40 wherein the external static compressional wave is caused by the infusion of a liquid or gas into the region being examined resulting in probing pressure changes.

51. A method according to 50 wherein the infusion of said liquid includes microbubbles.

52. A method according to 51 wherein said liquid is injected via one of a syringe and a catheter.

53. A method of detecting tumors according to claim 40 wherein the microbubbles introduced into the body are comprised of least two microbubble population types, each microbubble type having a distinct characteristics that contributes to combined spectrum wherein the presence of tumors, lesions, or abnormal growths is ascertained from changes in the combined spectral characteristics.

54. A method according to claim 53 wherein said microbubbles are comprised, at least in part, of any one of biocompatible gas, gel, and polymer material.

* * * * *

UNITED STATES PATENT AND TRADEMARK OFFICE
CERTIFICATE OF CORRECTION

Page 1 of 2

PATENT NO. : 5,749,364
DATED : May 12, 1998
INVENTOR(S) : Sliwa, Jr., et. al.

It is certified that error appears in the above-identified patent and that said Letters Patent is hereby corrected as shown below:

Column 2, Line 5, change the formula from
"$f=(1/\pi d)(3kP/p)^{1/2}$" to --$f = (1/\pi d)(3kP/\rho)^{1/2}$--

Column 2, Line 7, change "p" to --$\rho$--
Column 2, Line 46, change "representations" to --representations.--
Column 3, Line 5, change "the se" to --these--
Column 4, Line 65, change "B-ode" to --B-mode--
Column 5, Line 54, change "$f_c$" to --$f_c$--
Column 6, Line 14, change "$F_c$" to --$F_c$--
Column 6, Line 15, change "$2F_c$" to --$2F_c$--

Column 6, Line 57, change the formula from
"$f_0=(\frac{1}{2}\pi)(3\,y/p)^{1/2}(4\,\pi/3\,mR_mT)^{1/2}(P)^{5/6}$" to --$f_0 = (1/2\pi)(3\gamma/\rho)^{1/2}(4\pi/3mR_mT)^{1/2}(P)^{5/6}$--

Column 6, Line 59, change "y" to --$\gamma$--
Column 6, Line 60, change "p" to --$\rho$--
Column 6, Line 61, change "$R_m$" to --$R_m$--
Column 6, Line 64, change "$f_{nd}$" to --$f_{nd}$--

Column 6, Line 66, change the formula from
"$f_{nd}=(1/c)(2\,nf_tv\cos\theta)$" to --$f_{nd} = (1/c)(2nf_tv\cos\theta)$--

Column 7, Line 1, change "n=½,1,2,3," to --$n$=½,1,2,3,--
Column 7, Line 2, change "$f_t$" to --$f_t$--

UNITED STATES PATENT AND TRADEMARK OFFICE
CERTIFICATE OF CORRECTION

PATENT NO. : 5,749,364
DATED : May 12, 1998
INVENTOR(S) : Sliwa, Jr., et. al.

It is certified that error appears in the above-identified patent and that said Letters Patent is hereby corrected as shown below:

Column 7, Line 2, change "v" to --$v$--

Signed and Sealed this

Ninth Day of February, 1999

Attest:

Attesting Officer

*Acting Commissioner of Patents and Trademarks*